United States Patent
Harvill (10) Patent No.: US 9,279,773 B2
(45) Date of Patent: Mar. 8, 2016

(54) CRACK DETECTION AND MEASUREMENT IN A METALLURGICAL VESSELS

(71) Applicant: Process Metrix, Pleasanton, CA (US)

(72) Inventor: Thomas Lawrence Harvill, Alamo, CA (US)

(73) Assignee: PROCESS METRIX, Pleasanton, CA (US)

( * ) Notice: Subject to any disclaimer, the term of this patent is extended or adjusted under 35 U.S.C. 154(b) by 0 days.

(21) Appl. No.: 14/664,417

(22) Filed: Mar. 20, 2015

(65) Prior Publication Data
US 2016/0018341 A1     Jan. 21, 2016

Related U.S. Application Data

(60) Provisional application No. 62/026,052, filed on Jul. 18, 2014.

(51) Int. Cl.
*G01N 21/90* (2006.01)
*G01S 17/02* (2006.01)
*G01B 11/30* (2006.01)
*G01N 21/88* (2006.01)

(52) U.S. Cl.
CPC ............. *G01N 21/90* (2013.01); *G01B 11/303* (2013.01); *G01N 21/8806* (2013.01); *G01S 17/02* (2013.01)

(58) Field of Classification Search
CPC ....... G01S 17/88; G01S 17/023; G01N 25/72; G01N 21/90; G01B 11/06
USPC .......... 356/72–73, 601, 608, 609; 374/4, 137, 374/141, 142
See application file for complete search history.

(56) References Cited

U.S. PATENT DOCUMENTS

| | | | | |
|---|---|---|---|---|
| 4,172,661 A | * | 10/1979 | Marcus | G01C 15/00 356/141.1 |
| 4,508,448 A | * | 4/1985 | Scholdstrom | C21C 5/44 356/5.15 |
| 5,125,745 A | * | 6/1992 | Neiheisel | C21C 5/441 356/602 |
| 5,127,736 A | * | 7/1992 | Neiheisel | C21C 5/441 356/602 |
| 5,706,090 A | * | 1/1998 | Jokinen | F27D 21/0021 356/394 |
| 6,922,251 B1 | * | 7/2005 | Kirchhoff | C21C 5/44 356/601 |
| 7,164,476 B2 | * | 1/2007 | Shima | G01N 21/954 250/559.07 |
| 7,446,884 B2 | * | 11/2008 | Massen | G01B 11/24 250/334 |
| 7,924,438 B2 | * | 4/2011 | Kleinloh | F27D 21/0021 356/601 |
| 8,836,937 B2 | * | 9/2014 | Gutschow | G02B 23/2476 356/241.1 |
| 2013/0120738 A1 | * | 5/2013 | Bonin | G01N 25/72 356/72 |

* cited by examiner

*Primary Examiner* — Sang Nguyen
(74) *Attorney, Agent, or Firm* — Thomas Clinton; Donald M. Satina (57) ABSTRACT

Apparatuses, methods, and systems are disclosed to detect and measure cracks in the lining of a container. A typical apparatus includes a scanning device to acquire a cloud of data points by measuring distances from the scanning device to a plurality of points on the surface of lining material and a controller to fit a polygonal mesh and a minimum surface through the cloud of data points, a crack being detected by a portion of the polygonal mesh containing a connected group of polygons that extends past the minimum surface beyond a threshold distance.

21 Claims, 12 Drawing Sheets

| Direction | Max Depth(mm) | R (m) | Theta(°) | Z (m) | Length (mm) | Avg Width(mm) | Max Width (mm) |
|---|---|---|---|---|---|---|---|
| Vertical | 35 | 1.615 | 178.4 | 3.225 | 585 | 60 | 153 |
| Vertical | 27 | 1.564 | 205.7 | 1.825 | 582 | 80 | 244 |
| Vertical | 26 | 1.592 | 182.4 | 1.325 | 589 | 83 | 248 |
| Vertical | 26 | 1.569 | 307.8 | 2.6 | 1439 | 70 | 242 |
| Vertical | 25 | 1.572 | 174.4 | 1.775 | 561 | 60 | 138 |
| Vertical | 25 | 1.56 | 297.3 | 2.025 | 476 | 41 | 91 |
| Vertical | 24 | 1.571 | 311 | 1.525 | 775 | 73 | 254 |
| Vertical | 24 | 1.613 | 181.6 | 3.95 | 337 | 52 | 98 |
| Vertical | 23 | 1.541 | 287.7 | 1.95 | 490 | 77 | 218 |
| Vertical | 22 | 1.563 | 188 | 2.325 | 353 | 49 | 118 |
| Vertical | 21 | 1.546 | 34.6 | 2.225 | 265 | 35 | 70 |
| Vertical | 21 | 1.578 | 105.3 | 1.575 | 803 | 43 | 126 |
| Vertical | 21 | 1.538 | 188 | 0.75 | 454 | 65 | 187 |
| Vertical | 21 | 1.557 | 165.5 | 0.975 | 332 | 40 | 89 |
| Vertical | 20 | 1.576 | 209.7 | 4.502 | 347 | 54 | 149 |
| Vertical | 20 | 1.534 | 174.4 | 0.7 | 588 | 50 | 106 |
| Vertical | 20 | 1.586 | 214.6 | 1.9 | 777 | 43 | 90 |
| Vertical | 20 | 1.559 | 244.3 | 2.05 | 264 | 41 | 82 |
| Vertical | 19 | 1.576 | 356.8 | 3.325 | 701 | 46 | 106 |
| Vertical | 19 | 1.576 | 40.2 | 1.675 | 694 | 45 | 127 |
| Vertical | 19 | 1.527 | 168.8 | 0.725 | 456 | 43 | 105 |
| Vertical | 19 | 1.578 | 149.5 | 2.05 | 807 | 54 | 180 |
| Vertical | 19 | 1.576 | 203.3 | 4.155 | 791 | 63 | 165 |
| Vertical | 19 | 1.596 | 167.9 | 2.825 | 399 | 45 | 103 |
| Vertical | 19 | 1.574 | 196.1 | 4.022 | 374 | 41 | 86 |
| Vertical | 19 | 1.555 | 83.6 | 2.075 | 292 | 32 | 62 |
| Vertical | 18 | 1.567 | 175.2 | 2.35 | 410 | 53 | 122 |
| Vertical | 18 | 1.525 | 341.5 | 0.675 | 209 | 33 | 73 |
| Vertical | 18 | 1.573 | 64.3 | 1.775 | 314 | 37 | 79 |
| Vertical | 18 | 1.554 | 61.9 | 2.025 | 352 | 37 | 92 |
| Vertical | 17 | 1.571 | 341.5 | 2 | 335 | 47 | 104 |
| Vertical | 17 | 1.523 | 335.9 | 0.675 | 186 | 30 | 62 |
| Vertical | 17 | 1.561 | 358.4 | 2.3 | 634 | 33 | 70 |
| Vertical | 16 | 1.554 | 17.7 | 2 | 328 | 46 | 124 |
| Vertical | 16 | 1.559 | 11.3 | 1.975 | 379 | 46 | 134 |
| Vertical | 16 | 1.562 | 4 | 1.95 | 9783 | 143 | 411 |
| Vertical | 16 | 1.54 | 283.7 | 2.175 | 460 | 47 | 119 |
| Vertical | 16 | 1.58 | 211.3 | 3.725 | 364 | 44 | 115 |
| Vertical | 16 | 1.563 | 154.3 | 3.55 | 456 | 52 | 135 |
| Vertical | 15 | 1.591 | 56.3 | 0.95 | 227 | 35 | 80 |

Fig. 11

Fig. 12

CRACK DETECTION AND MEASUREMENT IN A METALLURGICAL VESSELS

CROSS REFERENCE TO RELATED APPLICATIONS

This application claims priority to U.S. Patent Application Ser. No. 62/026,052, filed on Jul. 18, 2014, entitled "Crack Detection and Measurement in Metallurgical Vessels," the contents of which are herein incorporated by reference in their entirety.

BACKGROUND

1. Technical Field

Embodiments of the subject matter disclosed herein relate generally to apparatuses, methods and systems and, more particularly, to devices, processes, mechanisms and techniques for detecting and measuring cracks in metallurgical vessels.

2. Description of Related Art

Metallic vessels or containers of various sizes and shapes designed to hold molten metals are widely used in many industrial applications. Example of these applications include, but are not limited to, gasification processes in chemical and power production, Electric-Arc Furnaces (EAF), Basic Oxygen Furnaces (BOF), ladles, blast furnaces, degassers, and Argon-Oxygen-Decarburization (AOD) furnaces in steel manufacturing. As known in the art, these containers are normally lined with refractory material installed in brick form or cast in monolithic blocks in order to protect the metallic part of the vessel from the high-temperature contents placed therein; however, due to normal wear and tear of the refractory material through the combined effects of oxidation, corrosion, and mechanical abrasion, some portion of the refractory surface in contact with the molten metal is lost during processing, thus requiring frequent inspection so as to assure extended use by performing early localized repair in order to avoid possible catastrophic failures and unnecessary or premature refurbishment of the entire vessel's refractory lining.

Figure 1:
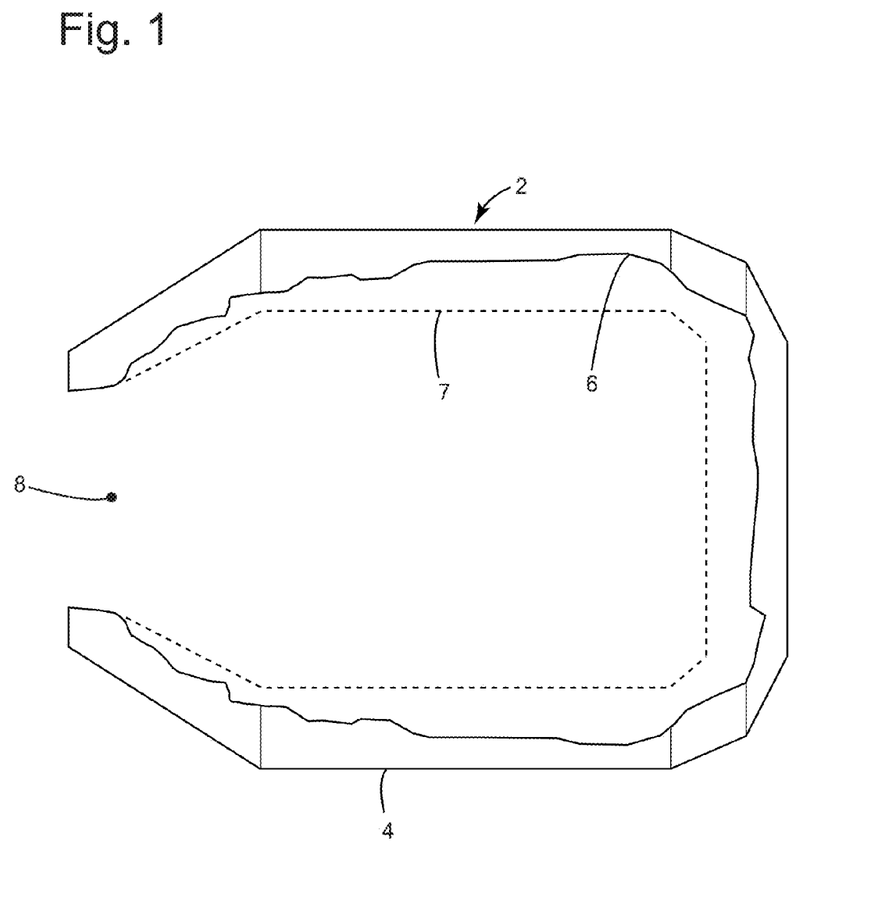
FIG. 1 illustrates a conventional metallurgical container having a refractory material protective layer.

FIG. 1 shows a conventional metallurgical container 2 having a shell 4, an internal layer of refractory material 6, and an opening 8. The dashed line 7 in FIG. 1 illustrates the original layer of refractory material before the container was placed in use. The difference between lines 7 and 6 is what existing systems are configured to detect in order for an operator to decide when to take the container out of service for repair. A specific wear pattern that creates potential hazards is cracks in the refractory material 6. Cracks allow molten metal to flow closer to the outer steel shell of the vessel 4, thereby creating increased probability of melting the shell 4. Melting the shell 4 is commonly referred to as "breakout" and is considerate by some to be a catastrophic failure mode that can cause significant damage and/or injury.

Initially characterization of the refractory thickness in these metallurgical containers was done visually by experienced operators. Given the hostile environment and the long downtime required that approach was quickly abandoned with the advent of automated systems. As understood by those of ordinary skill in the art, conventional automated processes are known to measure the localized thickness, i.e., the localized distance between the internal layer of refractory material 6 and the containers shell 4. A widely used conventional method for measuring the remaining lining thickness of metallurgical vessels is laser scanning.

Figure 2:
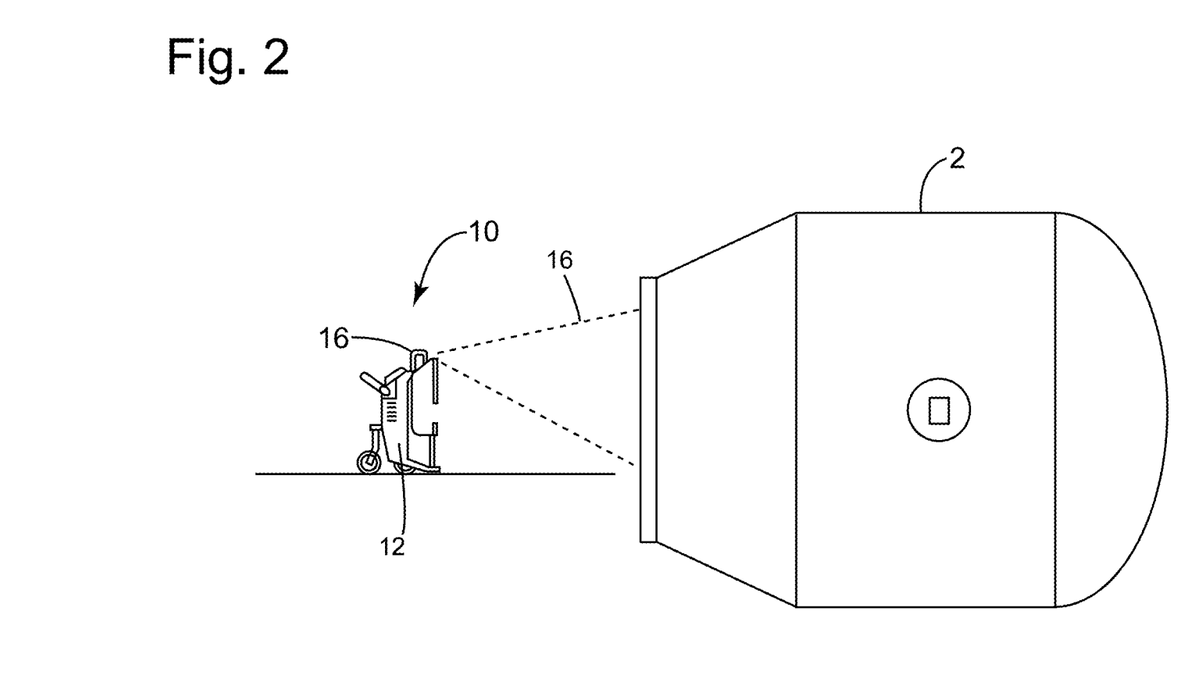
FIG. 2 illustrates a conventional laser scanning system to characterize the refractory material inside the container of FIG. 1.

FIG. 2 shows a conventional laser scanning refractory lining thickness measurement system 10 comprising a mobile cart 12, a laser scanning system 16 mounted thereon, and associated hardware and software located in the mobile cart 12. One of the goals of the laser scanning system 10 when used in metallurgical vessels is to accurately measure the lining thickness to allow a vessel to remain in service for as long as possible and to indicate areas requiring maintenance. A typical laser scanning system 14 includes a laser, a scanner, optics, a photodetector, and receiver electronics (not shown).

Such lasers are configured to fire rapid pulses of laser light at a target surface, some at up to 500,000 pulses per second. A sensor on the instrument measures the amount of time it takes for each pulse to bounce back from the target surface to the scanner through a given field of view 16 in FIG. 2. Light moves at a constant and known speed so the laser scanning system 14 can calculate the distance between itself and the target with high accuracy. By repeating this in quick succession the instrument builds up a complex 'map' of the surface it is measuring. By calculating and/or comparing changes between measured range maps of the internal surfaces of the refractory material 6 with reference measurement of the same surfaces, changes are detected and evaluated for possible changes that may result in a failure of the shell 4. Single measurements can be made in 20 to 30 seconds. An entire map of the furnace interior consisting of, for example, 4 to 6 measurements and more than 2,000,000 data points can be completed in a short time period (e.g., less than 10 minutes). Laser scanning produces a large collection of data points sometimes referred to as a cloud of data points.

However, despite the above-summarized progress in characterizing the wear on the refractory material 6 of the metallurgical container 2, to date no devices, processes, and/or methods exist that are capable of detecting and measuring a crack in the refractory surface 6. Therefore, based at least on the above-noted challenges with conventional laser scanning devices to characterize the integrity of vessels and to measure surface profiles thereof, it would be advantageous to have devices, methods, and systems capable of detecting, measuring, and/or characterizing cracks in the refractory material 6. Such a characterization would include the ability to quantify a maximum crack depth, location, orientation, length, average width, and maximum width. This information could then be presented to a knowledgeable user who would be able to determine the severity of a crack and evaluate if the metallurgical vessel requires maintenance or re-lining even before refractory scanning results in refractory wear below minimum safety levels.

SUMMARY

One or more of the above-summarized needs or others known in the art are addressed by apparatuses, methods, and processes to detect and measure cracks in the lining of a container. Such apparatuses include a scanning device to generate a cloud of data points by measuring distances from the scanning device to a plurality of points on the surface of the lining material of the container; and a controller connected to the scanning device, the controller being configured to fit a polygonal mesh through the cloud of data points and to fit a minimum surface through the cloud of data points, the crack being detected by a portion of the polygonal mesh containing a group of polygons that extends past the minimum surface beyond a threshold distance and the crack is measured by calculating a plurality of dimensions of the group of polygons.

Methods for detecting and measuring cracks in the lining of a container are also in the scope of the subject matter disclosed. Such methods include steps of fitting, using a controller, a polygonal mesh through a cloud of data points, the polygonal mesh having a resolution specified by a user and the cloud of data points being collected by a scanning device connected to the controller by measuring distances from the scanning device to a plurality of points on the surface of the lining material of the container; and fitting a minimum surface through the cloud of data points using the controller, wherein the crack is detected by a portion of the polygonal mesh containing a group of polygons that extends past the minimum surface beyond a threshold distance and the crack is measured by calculating a plurality of dimensions of the group of polygons.

BRIEF DESCRIPTION OF THE DRAWINGS

The accompanying drawings (not drawn to scale), which are incorporated in and constitute a part of the specification, illustrate one or more embodiments and, together with the description, explain these embodiments. In the drawings:

FIG. 10 illustrates a table showing various parameters and dimensions of cracks identified in FIG. 4 according to embodiments of the subject matter disclosed;

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of apparatuses, systems, or methods for detecting and measuring cracks in the refractory linings used to protect vessels or containers used in the metallurgical industry. However, the embodiments to be discussed next are not limited to these exemplary sets, but may be applied to other apparatuses, systems, or methods, including, but not limited to, the characterization, detecting, profiling, and/or measuring cracks on the lining of other containers configure to hold or transport substances having a temperature above the melting point of the materials of which the container is made.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures, or characteristics may be combined in any suitable manner in one or more embodiments.

This disclosure describes apparatuses, systems, and processes that analyze a cloud of data points obtained by scanning the refractory lining of a metallurgical vessel in order to identify cracks therein. Algorithms used then identify and quantify each crack in terms of the maximum crack depth, location, orientation, length, average width, and maximum width. A person of ordinary skill in the applicable arts can use this information to determine the severity of a crack and to evaluate if the metallurgical vessel requires maintenance or re-lining.

Figure 3:
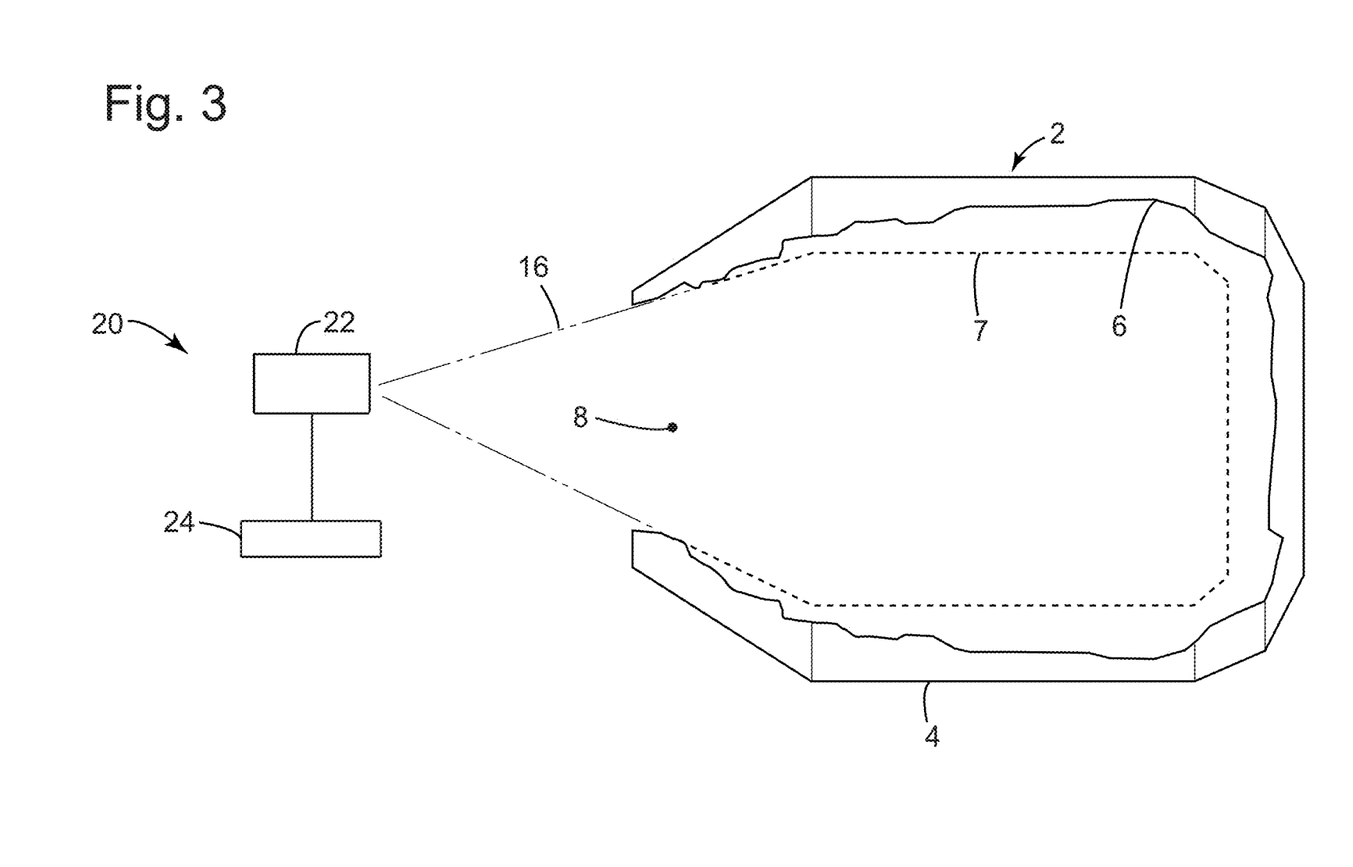
FIG. 3 illustrates an exemplary embodiment of a laser scanning system according to one aspect of the subject matter disclosed.

FIG. 3 illustrates an exemplary embodiment of a laser scanning system 20 capable of generating a cloud of data points according to one aspect of the subject matter disclosed. Generally speaking this laser scanning system 20 comprises two main components: a scanner 22 and a general controller 24. The laser scanning system 20 and general controller 24 may be disposed together in the same device or be separate from one another. For example, a mobile cart embodiment may include both in the same unit. In another embodiment, the laser scanner system 20 may be a unit by itself configured to be positioned in front of the container to be characterized and the general controller 24 be positioned in another location (for example, in the plant's operation control room). As used here, the general controller 24 may also be referred to as a data reduction device 24 and/or a computing or computer device 24.

In operation, through the field of view 16, the scanner 22 scans the refractory material 6 in the container 2, generating a cloud of data points to be transferred to the general controller 24. According to an embodiment, scanning data from the scanning system 20 are processed as now discussed. Note that in the field of characterizing the wear of metallurgical containers, there are existing processes for taking scanned data and applying various known processing steps in order to generate an image of the lining surface so as to identify areas in need of repair. Based on this image, which can be represented in print, on a screen, in a tabular way, etc., a metallurgical container expert determines whether repair to the lining of the container is needed and advises a metallurgical company accordingly. The embodiments discussed next improve this technological process of determining the worthiness of a metallurgical container by, for example, detecting and characterizing cracks in the lining material in order to improve the safety and to extend the container life.

In conventional systems this cloud of data points has hereto been used to characterize the wear in the refractory material 6. As those of ordinary skill in the art will appreciate, except to those noted and identified herein throughout, none of the features in the laser scanning system 20 and general controller 24 are to be considered limitations to the subject matter disclosed. In one embodiment, the laser scanning system 20 includes a laser, a scanner, optics, a photodetector, and receiver electronics. Many different types of lasers, scanners, optics, photodetectors, and receiver electronics exist that are capable of collecting a cloud of data points characterizing the surface of the refractory material 6. In one embodiment, the laser scanning system 20 is a specific implementation of a more general classification of measurement systems know as a LiDAR (Light Detection And Ranging OR Laser Imaging, Detection and Ranging system). In such embodiments, any type of LiDAR system is capable of producing the cloud of data points suitable for crack detection analysis if the precision of the device is at least half that of the feature sizes to be detected. Once acquired, the cloud of data points is transferred to the general controller 24 for further analysis, as will be further explained below. In one embodiment the laser scanning system 20 comprises an Anteris laser scanner, having a small (about 4 mm) beam diameter, high accuracy (±3 mm range error) scanning, large scanning rates (up to 500,000 Hz), a robust design suitable for the mill environment and the heat loads imposed during scanning high temperature surfaces, eye safe laser wavelength (which eliminates and/or substantially reduces workplace safety concerns), ±40° vertical scan angle, and 0-360° horizontal scan angle. Such a laser scanners allow standard resolution scans of a vessel interior in about 6 to 10 seconds, resulting in less vessel down time and higher production availability. In high-resolution mode, the Anteris scanner can provide detailed images of the vessel that can be used to detect cracks, define the region around a tap hole, or the condition of a purge plug.

Desirable characteristics of the scanner laser system 20 include time precision in order to provide desired levels of range accuracy, angular measurement precision, and beam sizes that will provide the desired overall precision as noted above. The minimum detectable feature size is dependent on the scanner's ability to spatially resolve an individual scanned point. Scanner uncertainty may be thought of as a sphere around a point with radius $\sigma_{Scanner}$. Using $\sigma_{Scanner}$ as the first standard deviation of the measurement uncertainty means there is 86% probability that the measured point is within the uncertainty sphere. Using this metric and heuristic data, the minimum feature size attainable, i.e., that can be seen, is twice the scanner uncertainty. This assertion is subject to the measurement resolution being less than or equal to the scanner uncertainty. The measurement resolution is the spatial separation of points on a measured surface. The measurement or scanner uncertainty is dominated by at least three terms, i.e., the range uncertainty ($\sigma_R$), the angular measurement uncertainty ($\sigma_{Angle}$), and the beam diameter uncertainty ($\sigma_B$). Assuming these are random variables, one can estimate the scanner uncertainty as the sum of the squares of range and angular uncertainties. Range uncertainty is dependent on the scanner's ability to measure range, hence a timing uncertainty (or $\delta t$). Angular uncertainty is dependent per point on the range to target (R), as:

$$\sigma_{Angle} = \sqrt{(R*\delta\phi)^2 + (R*\delta\theta)^2}. \quad (1)$$

And the scanner uncertainly, $\sigma_{Scanner}$, is then calculated by:

$$\sigma_{Scanner} = \sqrt{(\sigma_{Angle})^2 + (\sigma_R)^2 + (\sigma_B)^2}, \quad (2)$$

where, the beam uncertainty, $\sigma_B$, is equal to one half the beam diameter. With the above noted quantities, the minimum detectable crack size, or $\xi_{Crack,Min}$, is equal to twice the scanner uncertainty. In a practical system using a laser, the scanner uncertainty will often be limited by the beam size.

Generally speaking, once a cloud of data points is generated, cracks are detected and measured by initially fitting the cloud with a high-resolution polygonal mesh surface, $S_{HR}$, wherein said surface having, in some embodiments, a resolution defined or chosen by the user. As used herein throughout, the expression high resolution means average measurement point spacing on the surface in question of less than or equal to about 5 mm leading to a minimum detectable feature size of about 10 mm.

Subsequently, a minimum surface, $S_{min}$, is calculated for the cloud of data points. Comparison of $S_{HR}$ and $S_{min}$ will allow the identification of data points that are located at a distance greater than a specified distance from $S_{min}$, thereby identifying all points from $S_{HR}$ that possibly belong to cracks. As it will be further explained below, in one embodiment, such a comparison of $S_{HR}$ and $S_{min}$ is accomplished by identifying all facets from $S_{HR}$ that have vertexes that lie outside $S_{min}$, i.e., facets that are greater than a programmable distance from $S_{HR}$, thus generating a set of potential facets that belong to cracks in the refractory material 6. Finally, by further treatment of the vertexes that lie outside $S_{HR}$, connected facets are grouped into single cracks and crack characterization in terms of crack orientation, crack length, maximum crack depth location, average crack width, and maximum crack width is performed. Each of these portions of the subject matter disclosed will now be discussed in more details considering various embodiments.

Figure 4:
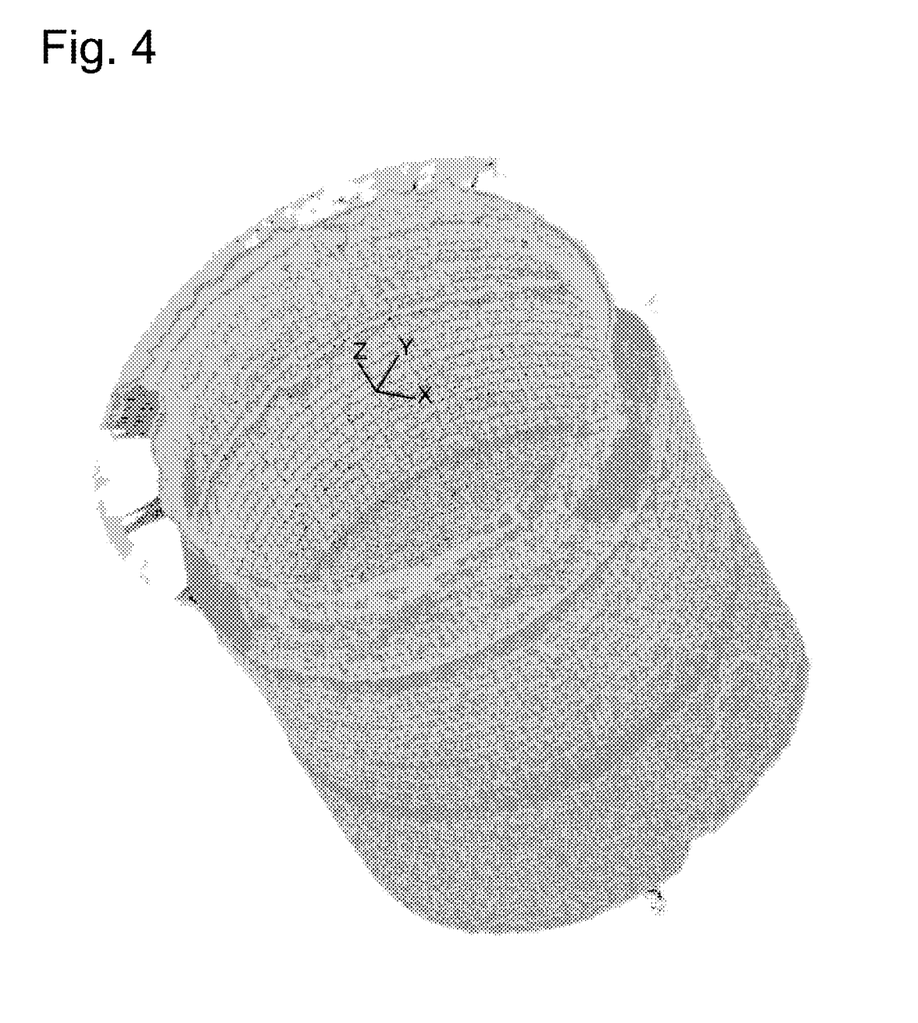
FIG. 4 illustrates a mesh representation of the container of FIG. 1 overlaid with a cloud of data points acquired with the system of FIG. 3 according to an embodiment of the subject matter disclosed.
Figure 5:
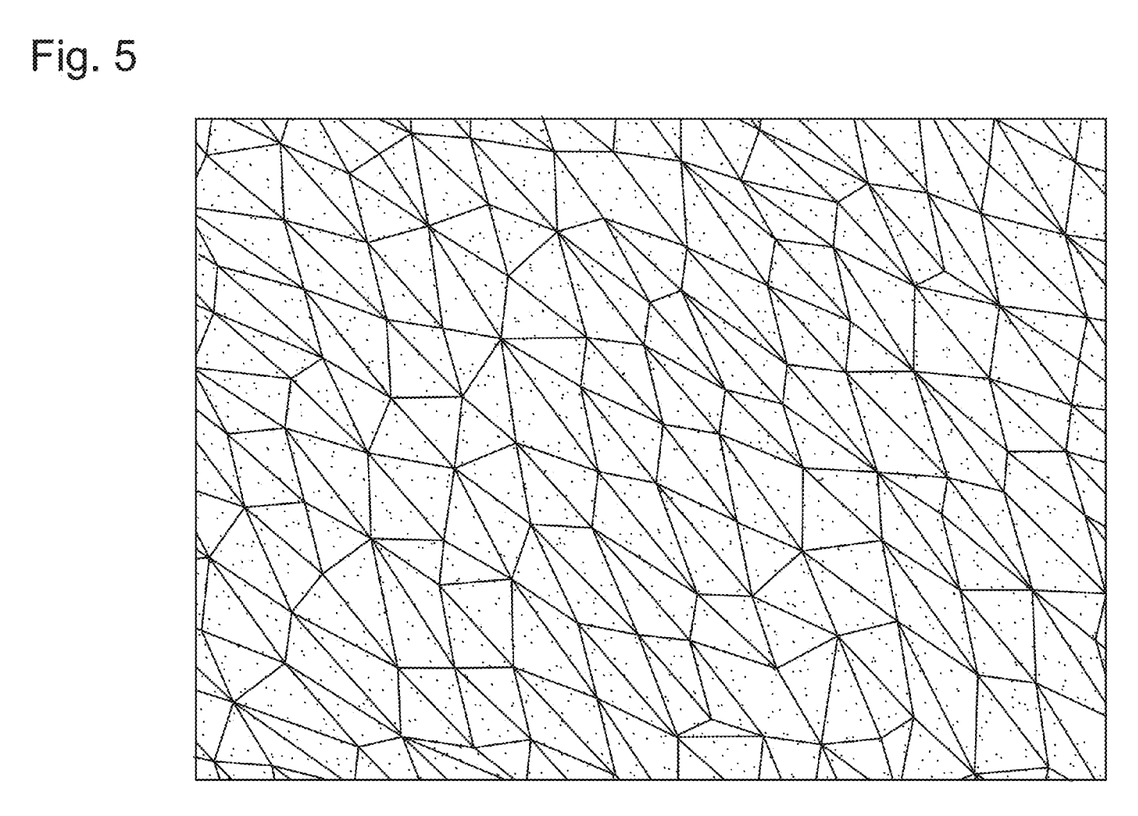
FIG. 5 illustrates a close-up of a portion of FIG. 4.

FIGS. 4 and 5 illustrate a high-resolution mesh representation of the metallurgical container generated from and overlaid with the cloud of data points acquired from the container with the scanning system of FIG. 3 according to an embodiment of the subject matter disclosed. FIG. 4 is an illustration of the entire container and FIG. 5 illustrates a close-up portion of FIG. 4. In the example given in FIGS. 4 and 5, a triangular mesh has been used. Nonetheless, those of ordinary skill will appreciate that other geometries could be used to generate such a mesh. In addition, the resolution of such a mesh is to be defined or selected by the user, as already noted; with the understanding that finer meshes will take more computational time to create and analyze than courser meshes. Also, the resolution may be selected according to the resolution of the cloud of data points—a higher density of data points leading to the ability to choose a finer mesh resolution. Therefore, the mesh size should be considerate as an arbitrary variable and not one that would limit the subject matter being disclosed herein.

In addition, in some embodiments, high-resolution scans are first obtained and the crack detention and characterization procedures described herein are then carried out. In other embodiments, low-resolution scans are first used to identify areas where possible cracks are located. Subsequently, high-resolution scans are then performed only of the area where possible cracks are located.

Generally speaking, the mesh size is larger than the accuracy of the light source being used to scan the container. For example, for a laser having an accuracy of ±5 mm, the resolution mesh size to be used may be chosen to be 25 mm. As noted, finer meshes may delay the data reduction process. For example, the data collected in FIG. 4 has about 1M+ data points per measurement. When converted into a data structure, using a triangular mesh in this example, all facets (i.e., each small triangle generated by fitting the data) have to be created. Therefore, the processing speed increases with the use of fewer triangles. For example, in a triangle mesh with 1M data points, for any type of mathematical operation (for example, creating a cross section of the mesh, calculating different desired volumes, or measuring different desired distances to various points), the computational time scales increase geometrically with the size of the structures. As such, as known by those of ordinary skill in the applicable arts, mesh size is an important computational constraint to be considered. Users expect close to real time results in order to be able to manipulate and look at calculated data, thus a balance between mesh size and computational time is always present.

Another consideration when generating the mesh is noise. The cloud of data points generated by the scanning system is noisy in nature and may also include acquired data that are statistical outliers, thus having to be removed since they do not belong to the surface being characterized. Different processes can be used to reduce noise in the scanned data. For example, a least-square fit may be used in order to reduce or filter out noise. In addition, crack detection and measurement are sensitive to the resolution selected by the user. For example, a crack on the order of 25 mm can be reliably detected using a laser with an accuracy of ±5 mm. If a selected grid size is equal to the crack size one desires to measure, it should be expected that such a crack might be detected but not quantified.

The gray surface illustrated in FIG. 4 is a surface resulting from a best-fit of all the data using a least-squares fit, i.e., $S_{HR}$, thus resulting essentially on a least-squares approximation of the raw cloud of data points. Limited by the resolution used to collect the raw cloud of data points, in order to better or more accurately fit the data to the crack features to be identified and characterized, the fitted mesh is refined to smaller polygonal elements (for example, triangular elements). The black dots shown in FIG. 5 are actual data points superimposed on the fitted surface shown. Thus, in some embodiments, the generated surface is a relatively small subsection of the whole. Throughout this disclosure, the surface illustrated in FIGS. 4 and 5 will be referred to as a high-resolution mesh surface, or $S_{HR}$.

Figure 6:
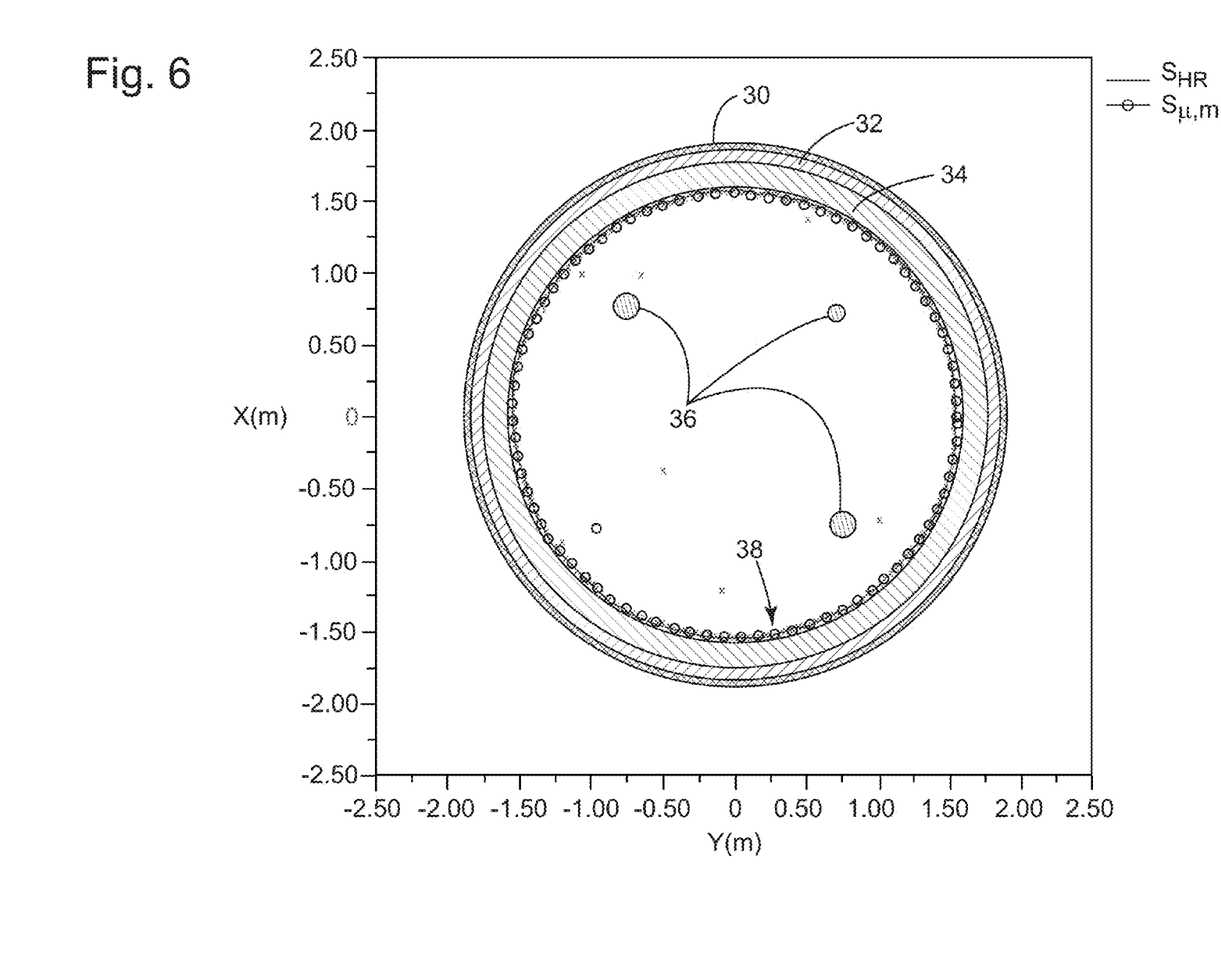
FIG. 6 illustrates a two-dimensional sectional view of the mesh representation fitted to the data points of FIG. 4 superimposed with a minimum surface fitted to the data points according to an embodiment of the subject matter disclosed.
Figure 7:
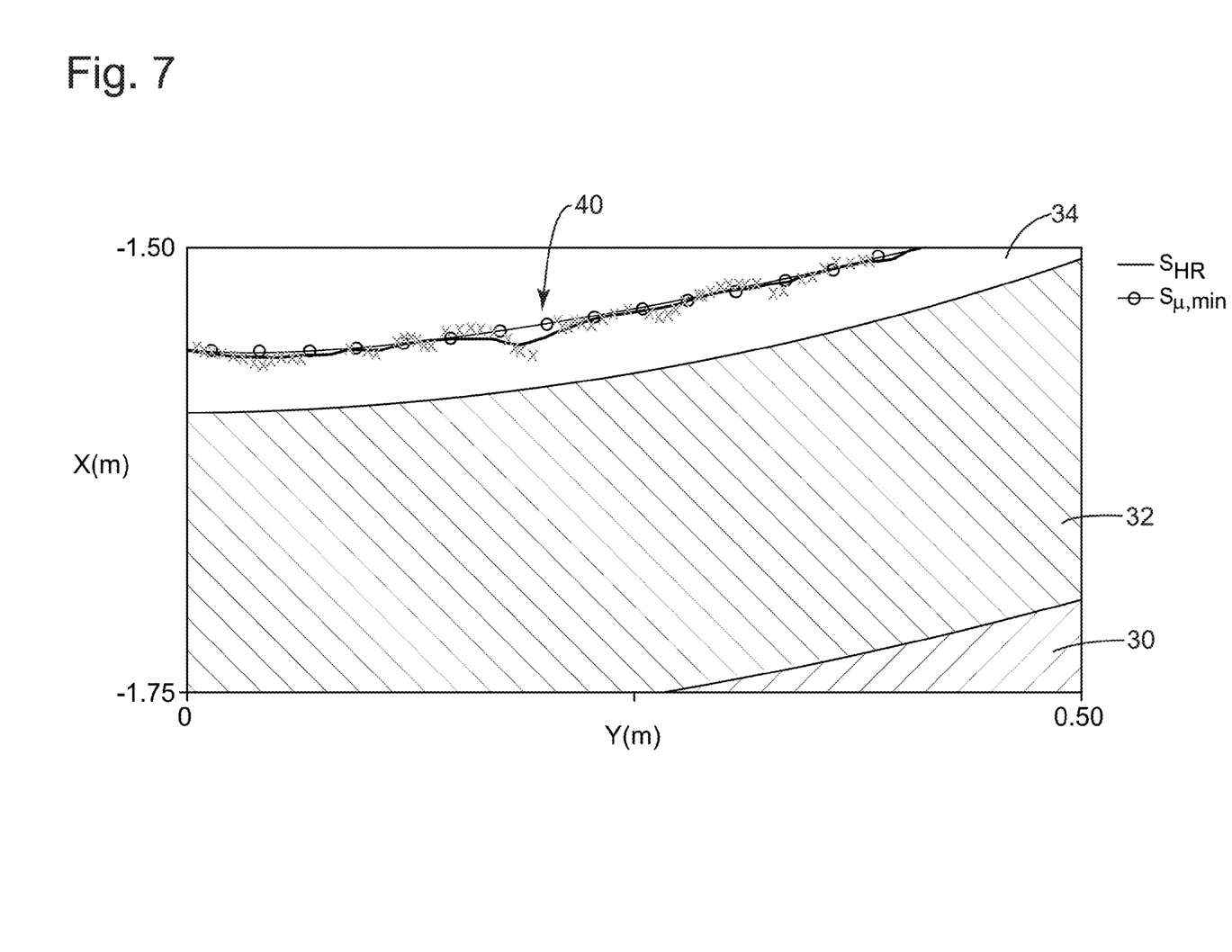
FIG. 7 illustrates a possible crack identified by a set of candidate facets of FIG. 6 according to an embodiment of the subject matter disclosed.
Figure 8:
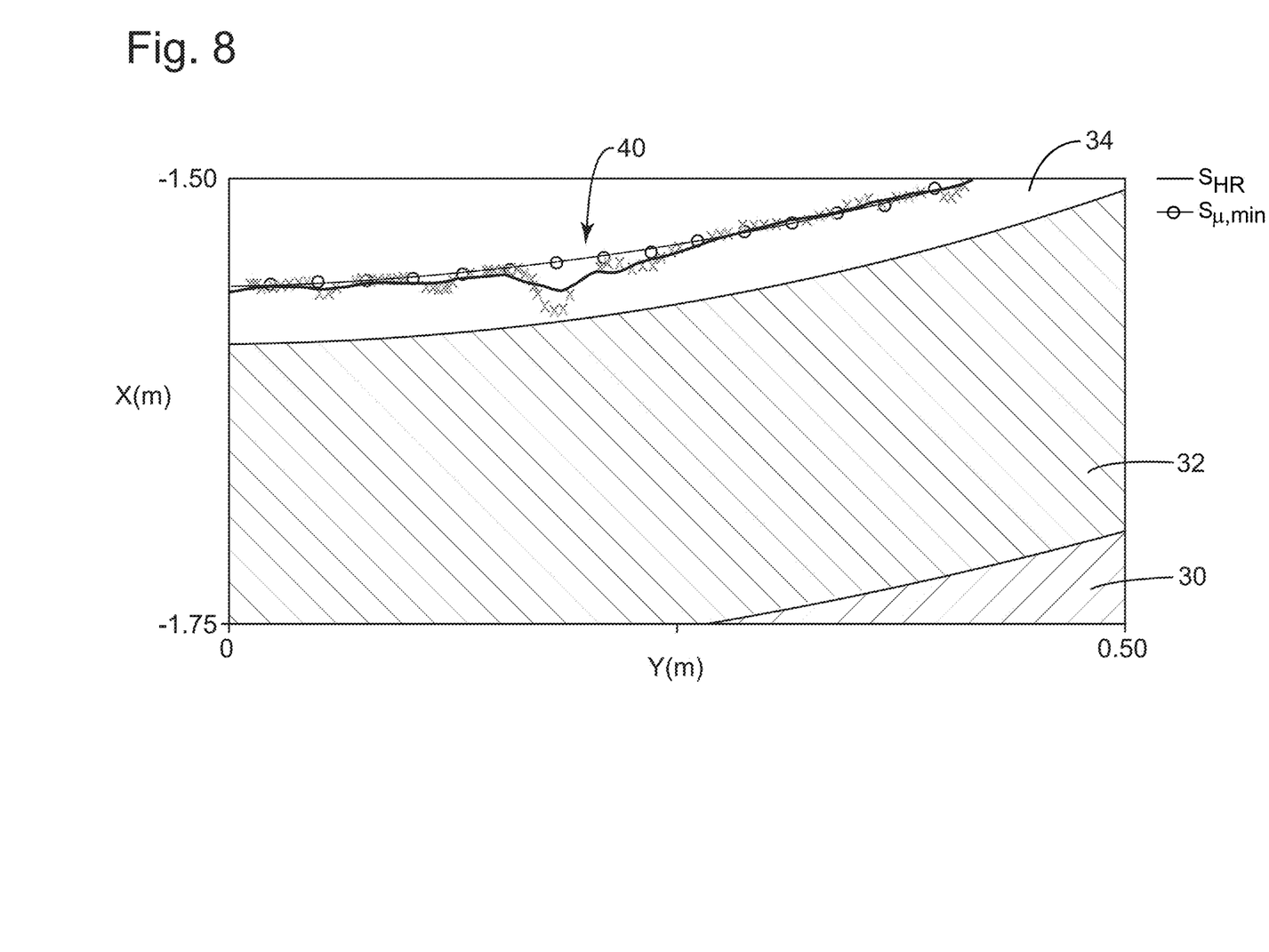
FIG. 8 illustrates another possible crack identified by a set of candidate facets of FIG. 6.

Once the high-resolution mesh surface, $S_{HR}$, is generated with a resolution defined by a user, the minimum surface, $S_{min}$, is calculated for the cloud of data points. Systematic comparison of $S_{HR}$ and $S_{min}$, will then allow the identification of data points that are located at a distance greater than a specified distance from the minimum surface, thereby identifying all points from $S_{HR}$ that are possibly associated to cracks. FIGS. 6-8 illustrate several full or partial two-dimensional sections of the data of FIG. 4, showing data points and both the high resolution and minimum surfaces.

The information generally illustrated in FIG. 6 is as follows. The steel shell encasing the container is shown at 30. A permanent lining 32 is disposed next to the shell 30, providing permanent protection thereto. Next to the permanent lining 32 is the layer of refractory material 6, sometimes referred to as the working lining 34. Cracks in the working lining 34 are the defects that one is usually concerned about. The holes 36 are either tapping holes used to pour out materials from the container and/or other holes used to stir or purge the container during material processing. In some scanning methods these features may be used as references to accurately position the container before measuring the working lining 34.

In one embodiment, $S_{HR}$ is a least-square best-fit and $S_{min}$ is the first negative standard deviation, µ, of $S_{HR}$, such a surface being hereinafter referred to as $S_{\mu,min}$. The high-resolution surface ($S_{HR}$), the minimum surface ($S_{min}$), and data points are shown at 38 next to the external surface of the working lining 34. In another embodiment, $S_{min}$ is a minimal surface constructed by subtracting from $S_{HR}$ the local negative standard deviation of $S_{HR}$. The least-square best-fit surface $S_{HR}$ may be thought of as the surface created by placing a blown balloon inside the container, but not so tight as to fit all cracks to be located and measured. In the magnified views shown in FIGS. 7 and 8, at 40, $S_{HR}$, $S_{\mu,min}$, and the actual data diverge, the best-fit showing a depression with the minimum surface located on top of it, thus identifying possible crack sites.

As understood by those of ordinary skill, there are different ways to remove noise and/or statistical outliers from the acquired data and to generate $S_{HR}$. For example, generation of such high-resolution mesh surface, $S_{HR}$, can be accomplished by techniques such as marching cubes, CRUST, and/or Poisson, to name just a few. As already indicated, a desired feature of such algorithms to enable viable crack detection is that the fitting algorithm be immune to noise. Noise immunity is a desired feature since the input point cloud is typically noisy for several reasons, including, but not limited to, scanner uncertainty and/or spuriously acquired data points from smoke, dust, and/or debris, which are also examples of statistical outlier data points. An advantageous fitting technique would employ a variable mesh size contingent on the level of detail of the cloud of data points. Those of ordinary skill in the applicable arts will understand that the resolution of such fitting techniques will affect the minimum size of the cracks to be detected and measured. For example, a 25-mm resolution will result in the accuracy of the crack calculation algorithm to be limited to roughly half this value, i.e., 12 mm. In addition, generation of the $S_{HR}$ surface may also be accomplished by processing the acquired data into smaller sets in order to improve speed while maintaining an acceptable data set size.

In embodiments using $S_{\mu,min}$, such a statistical representation of the fitted surface may be calculated such that for each facet, $F_I$, in the fitted surface $S_{HR}$, and for each point in the input cloud of data points, $P_J$, by the normal distance, $D_J$, from $P_J$ to $F_I$ is first calculated followed by determining the average normal distance $D_{I,AVG}$ and a standard deviation, $\sigma_I$, of all calculated normal distances. Subsequently, for each facet, $F_I$, in the fitted surface $S_{HR}$ and for each point in the input point cloud, $P_J$, $S_{\mu,min}$ can be calculated as follows:

$$\text{If } (D_J - D_{I,AVG}) < 0, \tag{3}$$
$$\text{add } D_J \text{ to } D_{mTOTAL} \text{ and increment a counter, } N_M;$$

$$D_{mAVG} = \frac{D_{mTOTAL}}{N_M}; \text{ and} \tag{4}$$

$$P_{ml} = \langle n_{FI}, D_{mAVG} \rangle, \tag{5}$$

wherein < > is the scalar product between the shown variables in which $n_{FI}$ is a unit vector normal to the facet $F_I$. Based on Equations (3)-(5), $S_{\mu,min}$ is then constructed from the points $P_{ml}$.

Cracks may be identified and measured by comparing $S_{HR}$ and $S_{\mu,min}$ once an operator-selected crack size is specified. Those of ordinary skill in the art will appreciate that a programmable distance is needed so as to control the amount of facets that will fit a condition designed to find cracks in order to characterize them. Cracks will only become significant when it has a given size. All facets that satisfy the operator-selected crack size are identified as possibly belonging to a crack. All such facets are set aside and later determined if they belong to the same group, that is, the same crack.

Cracks are initially filtered by extracting all facets, $F_I$, from the high-resolution mesh $S_{HR}$ that have any vertex that lie outside $S_{\mu,min}$ by a distance that is greater than a programmable distance, $\Omega_m$. These are all combined into a surface of crack candidates, or $S_{CC}$. In order to identify all facets that belong to a single crack, for all facets in $S_{CC}$, those with common vertices are connected into a surface of cracks, $S_C$, thereby creating a group $S_{RC,I}$ of I sub-surfaces ($S_{RC,J}$ is a sub-surface of $S_C$, which is a sub-surface of $S_{CC}$).

Mathematically, $S_C$ contains groups of connected facets from $S_{HR}$ that are crack surfaces, as such, for each vertex, $V_J$, in each facet, $F_I$, in the fitted surface $S_{HR}$, first the signed Euclidian distance, $D_{m,J}$, from $V_J$ to $S_{\mu,min}$ is calculated. Subsequently, If $D_{m,J} > \Omega_m$ then $F_I$ is added to the surface of candidate cracks, $S_{CC}$, wherein $\Omega_m$ is the user-selected programmable parameter. Afterwards, one recursively groups facets in $S_{CC}$ with those facets having any common vertices, thereby forming groups into the raw crack surface $S_{RC,I}$. Groups in $S_{RC,I}$ are recursively grouped to form $S_C$ by combining surfaces in $S_{RC,I}$ if a minimal distance between surfaces, $D_{RC}$, and another programmable parameter, $\Omega_C$, is satisfied. $\Omega_C$ can be thought of as a physical distance such that, if one has two cracks that are "close" (within $\Omega_C$) and pointing in the same direction, then they can be considered the same crack, thus creating the crack surface collection, $S_C$.

Statistics for each crack are then calculated with the information in $S_C$. That is, in one embodiment, the Euclidian distance from each vertex in $S_C$ to $S_{\mu,min}$ may determine the average crack depth, $D_{CAVG}$. The maximum crack depth, $D_{CMAX}$, and the crack location may be determined in another embodiment by the maximum Euclidian distance from each vertex in $S_C$ to $S_{\mu,min}$. Finally, fitting a least-square, best-fit line through all vertices in one crack may be used to determine crack orientation, which should correspond to the direction of the best-fit line.

Another way to quantify the detected and measured cracks is to determine their orientation. Orientation is a desirable characteristic because of the way certain vessels are constructed. Depending on the construction characteristics of a given vessel, cracks are most likely to occur along brick lines. Knowing the main orientation that, for example, the refractory material may have been disposed, one may search and characterize cracks that are substantially aligned with that main orientation depending on a particular application. Those of ordinary skill in the applicable arts will appreciate that the apparatuses, systems, methods, and processes being disclosed are general. As such, one is capable to search for a certain direction or facets grouped together along such a direction. In addition, experienced gain in working with certain types of vessels and their refractory materials, best programmable orientation may be decided by experience, type of application, how bricks were laid, orientation selected as function of type of brick, and/or expected type of crack in a given application, to name just a few examples.

For example, if vertical cracks are somehow prevalent in a given application, cracks within, for example, ±30° of a vertical axis (for example, a Z-axis) having a length-to-average-width ratio, or $R_{L/W}$, greater than a minimum programmable threshold value, or $R_{L/W,MIN}$, may be searched for in the reduced data. Similarly, if horizontal cracks are somehow prevalent in another application, cracks within, for example, ±30° of a horizontal plane (for example, a XY plane) having a length-to-average-width ratio, $R_{L/W}$, greater than a minimum programmable threshold value, or $R_{L/W,MIN}$, may then be identified in the reduced data.

For each $S_{RC,I}$ in $S_{RC}$, one determines the length, orientation, maximum depth, average width, maximum width, and location by first connecting to other $S_{RC,IJ}$ sub-surfaces to create a new consolidated sub-surface set $S_{C,I}$. $S_{RC,I}$ should have the same orientation as $S_{RC,J}$. $S_{RC,I}$ should be within a maximum distance $\Omega_C$, from $S_{RC,J}$. And, finally, $S_{RC,IJ}$ should have a higher length-to-average-width ratio than $S_{RC,I}$ and $S_{RC,J}$, i.e., $R_{L/W,I} > R_{L/W,J}$. For each facet in $S_C$, one calculates the crack depth. Crack depth is defined as the maximum Euclidian distance between each vertex in $S_{C,I}$ and $S_{\mu,min}$. To improve depth calculation accuracy algorithms within the scope of the subject matter disclosed can optionally re-fit $S_{HR}$ only in the region defined by $S_{C,I}$ to create a fitted surface having a resolution higher than the one first employed.

Those of ordinary skill will appreciate that $S_{RC,I}$ is the subgroup that has satisfied the given filtering criteria, but they may not be connected to other subgroups directly—they actually touch one another. So one may detect a crack or possibly a lump of processing materials that may have a filled crack in a small portion thereof. The last processing steps just described are therefore an evaluation of a proximity criterion that would be set to group the subgroups into super subgroups. If they are close enough and roughly follow the same orientation they are the same crack. As such, $\Omega_C$ allows for filling materials, and, after the first grouping, the proposed processes will check again based now on all cracks that have satisfied all conditions. In the given explanation, i is for all groups that have satisfied the given criteria and j is for all. Those of ordinary skill will appreciate that i cannot be equal j because, if so, the given condition would be satisfied every time—clearly an undesirable outcome.

As those of ordinary skill will appreciate, a length-to-average-width ratio is an desirable variable to consider and one that should be chosen depending on the type of application being examined and the characteristics of what types of cracks are being sought. Once a value for this variable is specified and the data filtered, all possible candidates that fit the set criteria will be taken and the user may, for example, fit a best-fit line through all of those facets—effectively putting a bounding box around the selected facets. For this set, if a group of facets has a length-to-width-ratio of about one, for example, it is a crater and not a crack. A crack will usually be characterized by a long longitudinal dimension relative to a transverse dimension. As such, by being able to specify a length-to-average-width ratio the products, processes, and systems being disclosed will have a built-in flexibility. Typically a ratio of about 4 may be specified, but will depend on the type of application and other variables known to those of ordinary skill. For example, cracks in ladles may have a length-to-average-width ratio that is probably greater than 4. In other application, users may want to look for very large cracks, sometimes even craters, like a position where a brick has fallen out—a large whole. So one of the advantageous features of the products, processes, and systems being disclosed is the flexibility in setting a length-to-average-width ratio as a function of what is being sought or the application at hand.

Figure 9:
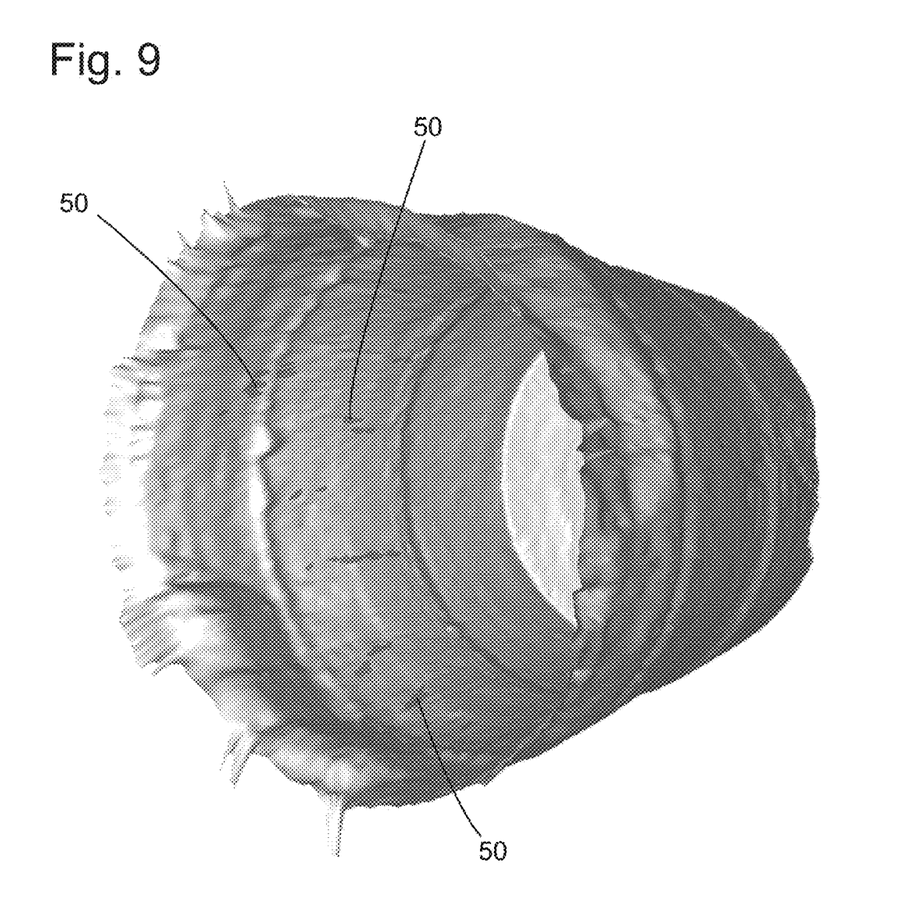
FIG. 9 illustrates a three-dimensional representation of detected cracks according to an embodiment of the subject matter disclosed.

The darker regions identified as 50 in FIG. 9 illustrate cracks in the container of FIG. 4. These cracks have been detected and characterized as a result of the above-discussed procedures and/or calculations carried out on the cloud of data points illustrated in the same figure. The table in FIG. 10 illustrates values, for each detected crack, of crack orientation, maximum depth, location in cylindrical coordinates (radius (R), angle (θ), and longitudinal distance (Z)), crack length, average width, and maximum width.

Figure 11:
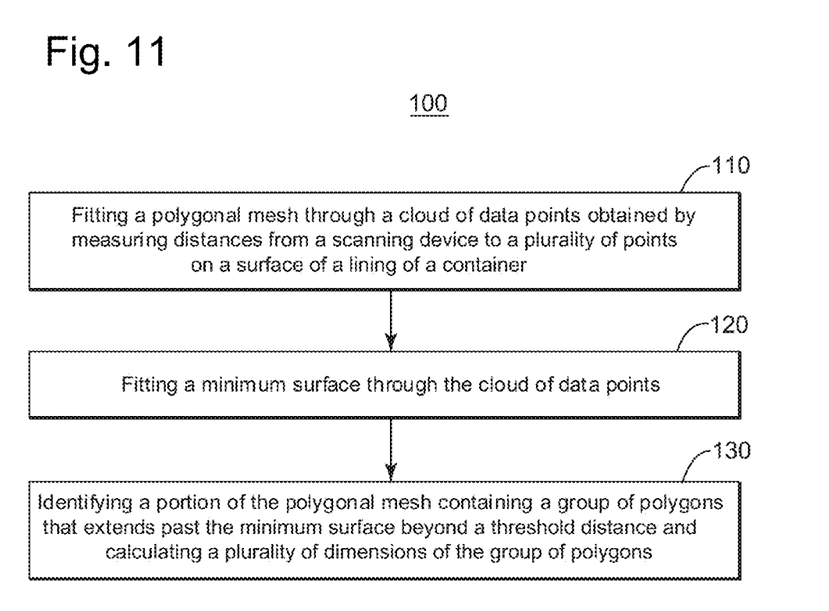
FIG. 11 illustrates a flowchart of a method according to an embodiment of the subject matter disclosed.

Methods and processes configured to detect/identify, measure, and characterize cracks in the lining of a vessel or container are also within the scope of the subject matter disclosed. FIG. 11 illustrates the flowchart of an exemplary embodiment of a method or process 100 according to the subject matter disclosed. As shown, at 110, such methods include fitting a polygonal mesh through a cloud of data points, the polygonal mesh having a resolution specified by a user, the cloud of data points being collected by a scanning device by measuring distances from the scanning device to a plurality of points on the surface of the lining material of the container. At 120, fitting a minimum surface through the cloud of data points using the controller. And, at 130, identifying/detecting a crack by a portion of the polygonal mesh containing a group of polygons that extends past the minimum surface beyond a threshold distance selected by the user and measuring a plurality of dimensions of the group of polygons.

Figure 12:
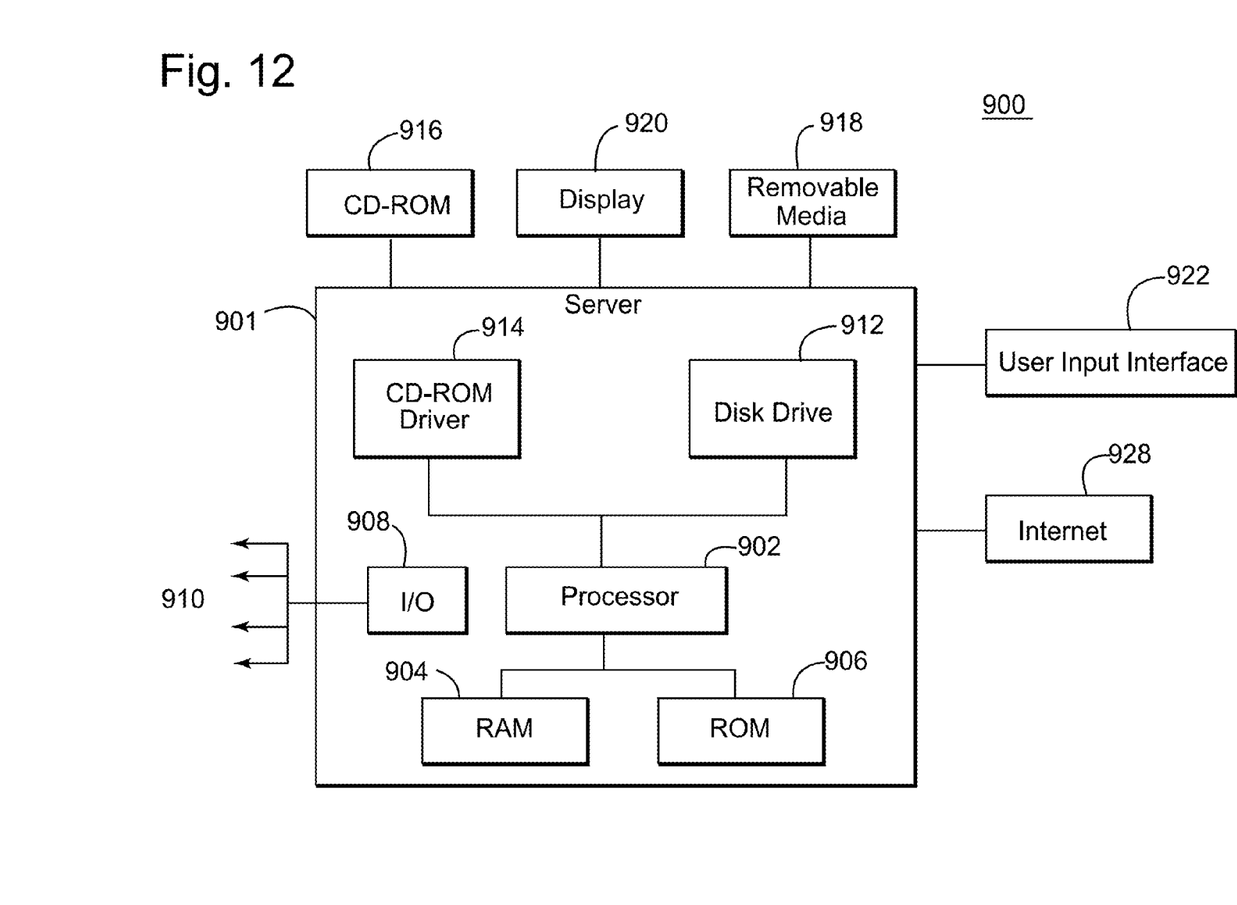
FIG. 12 illustrates a computer system configured to identify and characterize cracks in the container of FIG. 1 according to an embodiment of the subject matter disclosed.

One or more of the steps of the methods comprising the subject matter disclosed may be implemented in a computing system specifically configured to detect/identify, measure, and characterize cracks in the refractory lining of a metallurgical vessel or container as explained hereinabove. An example of a representative computing system capable of carrying out operations in accordance with the exemplary embodiments is illustrated in FIG. 12. Hardware, firmware, software or a combination thereof may be used to perform the various steps and operations described herein.

The exemplary computing system 900 suitable for performing the activities described in the exemplary embodiments may include a server 901. Such a server 901 may include a central processor (CPU) 902 coupled to a random access memory (RAM) 904 and to a read-only memory (ROM) 906. The ROM 906 may also be other types of storage media to store programs, such as programmable ROM (PROM), erasable PROM (EPROM), etc. The processor 902 may communicate with other internal and external components through input/output (I/O) circuitry 908 and bussing 910 to provide control signals and the like. The CPU 902 carries out a variety of functions as is known in the art, as dictated by software and/or firmware instructions.

The server 901 may also include one or more data storage devices, including a disk drive 912, CD-ROM drives 914, and other hardware capable of reading and/or storing information such as a DVD, etc. In one embodiment, software for carrying out the above-discussed steps may be stored and distributed on a CD-ROM 916, removable memory device 918 or other form of media capable of portably storing information. These storage media may be inserted into, and read by, devices such as the CD-ROM drive 914, the disk drive 912, etc. The server 901 may be coupled to a display 920, which may be any type of known display or presentation screen, such as LCD displays, LED displays, plasma display, cathode ray tubes (CRT), etc. A user input interface 922 is provided, including one or more user interface mechanisms such as a mouse, keyboard, microphone, touch pad, touch screen, voice-recognition system, etc.

The server 901 may be coupled to other computing devices, such as the landline and/or wireless terminals via a network. The server may be part of a larger network configuration as in a global area network (GAN) such as the Internet 928, which allows ultimate connection to the various landline and/or mobile client devices.

The disclosed exemplary embodiments provide apparatuses, methods, and systems for detecting/identifying, measuring, and characterizing cracks in the lining of a metallurgical vessel or container as well the other uses hereinabove summarized and appreciated by those of ordinary skill in the applicable arts after consideration of the subject matter disclosed. It should be understood that this description is not intended to limit the invention. On the contrary, the exemplary embodiments are intended to cover alternatives, modifications and equivalents, which are included in the spirit and scope of the invention as defined by the appended claims.

Further, in the detailed description of the exemplary embodiments, numerous specific details are set forth in order to provide a comprehensive understanding of the claimed invention. However, one skilled in the art would understand that various embodiments might be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

While the disclosed embodiments of the subject matter described herein have been shown in the drawings and fully described above with particularity and detail in connection with several exemplary embodiments, it will be apparent to those of ordinary skill in the art that many modifications, changes, and omissions are possible without materially departing from the novel teachings, the principles and concepts set forth herein, and advantages of the subject matter recited in the appended claims. Hence, the proper scope of the disclosed innovations should be determined only by the broadest interpretation of the appended claims so as to encompass all such modifications, changes, and omissions. In addition, the order or sequence of any process or method steps may be varied or re-sequenced according to alternative embodiments. Finally, in the claims, any means-plus-function clause is intended to cover the structures described herein as performing the recited function and not only structural equivalents, but also equivalent structures.

What is claimed is:

1. An apparatus configured to detect and measure a crack on a surface of a lining of a container, said apparatus, comprising:
    a scanning device having a laser, optics, a scanner, a photodetector, and receiver electronics, the scanning device being configured to generate a cloud of data points by measuring distances from the scanning device to a plurality of points on the surface of the lining of the container; and
    a controller connected to the scanning device, the controller being configured to fit a polygonal mesh through the cloud of data points using a resolution selected by a user, and, to fit a minimum surface through the cloud of data points, wherein the crack is detected by a portion of the polygonal mesh containing a group of polygons that extends past the minimum surface beyond a threshold distance selected by the user and the crack is measured by calculating a plurality of dimensions of the group of polygons.

2. The apparatus according to claim 1, wherein the controller is further configured to remove statistical outliers from the cloud of data points before fitting the polygonal mesh and the minimum surface.

3. The apparatus according to claim 1, wherein the polygonal mesh is obtained by a least-square, best-fit of the cloud of data points and the minimum surface is a first negative standard deviation of the least-square, best fit.

4. The apparatus according to claim 1, wherein the minimum surface is calculated by calculating a normal distance from each facet of the polygonal mesh to each point in the cloud of data points and determining an average normal distance and a standard deviation of the calculated normal distances, wherein, for each facet in the fitted polygonal surface and for each point in the input point cloud, the minimum surface is calculated by scalar products between unit vectors normal to corresponding facets and the calculated normal average.

5. The apparatus according to claim 1, wherein the threshold distance is a function of an industrial application of the container and/or a size of the crack.

6. The apparatus according to claim 1, wherein an average crack size is determined by averaging distances from each facet of each polygon in the connected group of polygons and a maximum crack depth is calculated by determining a maximum distance from the distances of each vertex of the polygon in the connected group of polygons to the minimum surface.

7. The apparatus according to claim 1, wherein the controller is located in a control room of an industrial facility where the container is located separate from the scanning device.

8. The apparatus according to claim 1, wherein a resolution of the scanning device is equal to or less than about one half of a characteristic dimension of the crack being measured.

9. The apparatus according to claim 1, wherein the plurality of dimensions includes an orientation of the crack with respect to the container.

10. The apparatus according to claim 9, wherein an angular range for the orientation is specified and only cracks having a length-to-average-width ratio greater than a minimum threshold value are identified.

11. A method for detecting and measuring a crack on a surface of a lining of a container, said method, comprising:
fitting a polygonal mesh through a cloud of data points, the polygonal mesh having a resolution specified by a user and the cloud of data points being collected by a scanning device by measuring distances from the scanning device to a plurality of points on the surface of the lining material of the container; and
fitting a minimum surface through the cloud of data points, wherein the crack is detected by a portion of the polygonal mesh containing a group of polygons that extends past the minimum surface beyond a threshold distance selected by the user and the crack is measured by calculating a plurality of dimensions of the group of polygons.

12. The method according to claim 11, further comprising:
filtering statistical outliers out of the cloud of data points before the fitting of the polygonal surface and the fitting of the minimum surface.

13. The method according to claim 11, wherein the fitting of the polygonal mesh further comprises:
fitting a least-square, best-fit of the cloud of data points and the fitting of the minimum surface comprises a calculation of a first negative standard deviation of the least-square, best fit of the cloud of data points.

14. The method according to claim 11, wherein the fitting of the minimum surface further comprises:
calculating a normal distance from each facet of the polygonal mesh to each point in the cloud of data points; and
determining an average normal distance and a standard deviation of the calculated normal distances, wherein, for each facet in the fitted polygonal surface and for each point in the input point cloud, the minimum surface is calculated by scalar products between unit vectors normal to corresponding facets and the calculated normal average.

15. The method according to claim 11, further comprising:
calculating an average crack size by averaging distances from each facet of the polygon in the connected group of polygons to the minimum surface; and
calculating a maximum crack depth by determining a maximum distance from the distances from each vertex of the polygon in the connected group of polygons to the minimum surface.

16. The method according to claim 11, wherein the polygonal mesh is a triangular mesh.

17. The method according to claim 11, wherein a resolution of the scanning device is equal to or less than one half of a characteristic dimension of the crack being measured.

18. The method according to claim 11, further comprising:
separating cracks in the group of polygons by groups of polygons having common vertices or common directions.

19. The method according to claim 11, wherein the plurality of dimensions includes an orientation of the crack with respect to the container.

20. The method according to claim 19, wherein an angular range for the orientation is specified and only cracks having a length-to-average-width ratio greater than a minimum threshold length-to-average-width ratio value are identified.

21. The method according to claim 20, where the length-to-average-width ratio and the minimum threshold value are a function of an industrial application of the container.

* * * * *